United States Patent

Zinner et al.

[11] Patent Number: 5,990,305
[45] Date of Patent: Nov. 23, 1999

[54] PHOTOCHROMIC DIARYL-3H-NAPHTHOPYRANE

[75] Inventors: Herbert Zinner, Pentling; Manfred Melzig, Wessling, both of Germany

[73] Assignee: Optische Werke G. Rodenstock, Munich, Germany

[21] Appl. No.: 08/875,209

[22] PCT Filed: Oct. 28, 1996

[86] PCT No.: PCT/DE96/02049

§ 371 Date: Feb. 2, 1998

§ 102(e) Date: Feb. 2, 1998

[87] PCT Pub. No.: WO97/15565

PCT Pub. Date: May 1, 1997

[30] Foreign Application Priority Data

Oct. 28, 1995 [DE] Germany .............. 195 40 185

[51] Int. Cl.⁶ .............. B07D 311/92; B07D 405/04; B07D 407/04; B07D 409/04; C08K 5/15; C09K 9/00

[52] U.S. Cl. .............. 540/480; 544/61; 544/150; 546/144; 546/167; 546/196; 548/311.4; 548/427; 548/465; 548/525; 548/962; 549/389

[58] Field of Search .............. 549/389; 544/61, 544/150; 540/480; 546/144, 167, 196; 548/311.4, 427, 465, 525, 962

[56] References Cited

U.S. PATENT DOCUMENTS

| | | | |
|---|---|---|---|
| 3,567,605 | 3/1971 | Becker | 204/158 |
| 5,066,818 | 11/1991 | Gemert et al. | 549/389 |
| 5,274,132 | 12/1993 | VanGemert | 549/389 |
| 5,369,158 | 11/1994 | Knowles | 524/1.1 |
| 5,411,679 | 5/1995 | Kumar | 252/586 |
| 5,656,206 | 8/1997 | Knowles et al. | 252/586 |
| 5,658,500 | 8/1997 | Kumar et al. | 252/586 |
| 5,658,501 | 8/1997 | Kumar et al. | 252/586 |

FOREIGN PATENT DOCUMENTS

| | | |
|---|---|---|
| 0 313 941 | 5/1989 | European Pat. Off. . |
| 0629620 | 12/1994 | European Pat. Off. . |

OTHER PUBLICATIONS

Momota et al, Chemical Abstracts, vol. 125, No. 15, #195483Z, 1996.

Matsuoka et al, Chemical Abstracts, vol. 125, No. 17, #221584V, 1996.

*Primary Examiner*—Floyd D. Higel
*Attorney, Agent, or Firm*—Antonelli, Terry, Stout & Kraus, LLP

[57] ABSTRACT

Disclosed is a photochromic compound having a diaryl-3H-napthopyran structure, which has at the 8-position a nitrogen atom-linked hetercyclus, in which the heterocylcus can also have a HALS compound as a substituent or the heterocyclus itself can be formed as a HALS compound.

Furthermore a photochromic compound is described having a diaryl-3H-naphtopyran structure which has at the 8-position an N-atom linked and an alkyl-bridge linked HALS compound.

20 Claims, No Drawings

PHOTOCHROMIC DIARYL-3H-NAPHTHOPYRANE

This application is a national stage application (371) of PCT/DE96/02049, filed on Oct. 28, 1996.

TECHNICAL FIELD

The present invention relates to photochromic diaryl-3H-naphthopyrans.

STATE OF THE ART

Photochromic compounds possess the property that they change color reversibly under the influence of light containing a certain amount of ultra-violet radiation, such as for instance sunlight or the light from a mercury vapor lamp. This coloring is due to a bond opening in the pyran ring of the photochromic naphthopyran induced by the high-energy ultra-violet light. After removing the ultraviolet radiation source, the compound returns to its original closed state.

A variety of classes of photochromic compounds have been known for some time and are used in various applications requiring reversible light-dependent coloring, by way of illustration by means of the ultraviolet part of the sunlight.

A variety of methods for coloring plastic articles using photochromic compounds are described in the state of the art. With regard to this reference is made, by way of example, to U.S. Pat. No. 4,286,957, DE-A 35 16 568 and EP 0 227 337 B1.

The basic chemical structure of benzopyrans and naphthopyrans is described by Becker in U.S. Pat. No. 3,567,605. However these compounds, which were patented as early as in 1971, are hardly of significance for use in the production of photochromic articles, because their color is dependent on irradiation with ultraviolet light only at temperatures in the −40° C. range.

Moreover, U.S. Pat. No. : 5,066,818 discloses that photochromic compounds that are suited for use at normal temperatures are obtained by introducing at least one ortho-substituted phenyl group in the 3H-position of the pyran ring. These compounds can be employed, by way of illustration, in optical lenses or other transparent plastic articles.

A further development of the general naphthopyran compounds known from U.S. Pat. No. 5,066,818 is described in U.S. Pat. No. 5,369,158. According to this printed publication, the photochromic naphthopyrans possess particularly advantageous properties if they are substituted at the 8-position of the naphthalene portion. Compared to other naphthopyrans with substitutents in the 5-, 7- or 9- position, these photochromic compounds exhibit a considerable bathochromic shift of the absorption maximum in the activated as well as in the non-activated state. Furthermore, this shift leads to increased darkening velocity and greater optical density in the photochromic compound.

The naphthopyrans of U.S. Pat. No. 5,369,158 have the following structure:

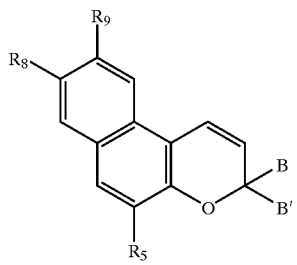

with R5 and R9 being H, $C_1$–$C_4$ alkoxy or $C_1$–$C_4$ alkyl, R8 being halogen, $C_1$–$C_5$ acyloxy, benzoyloxy, methoxybenzoyloxy or di($C_1$–$C_5$)alkylamino or LO-, wherein L is $C_1$–$C_{12}$ alkyl, $C_6$–$C_9$ aryl ($C_1$–$C_3$) alkyl, $C_5$–$C_7$ cycloalkyl or $C_5$–$C_7$ cycloalkyl substituted by $C_1$–$C_4$ alkyl and B and B' are substituted or unsubstituted phenyl or naphthyl, pyridyl, thienyl, benzothienyl, furyl or benzofuryl, with the substituent or substituents being $C_1$–$C_4$ alkyl, $C_1$–$C_4$ halogen alkyl, $C_1$–$C_4$ alkoxy, $C_1$–$C_4$-alkoxy($C_1$–$C_4$) alkyl, di ($C_1$–$C_5$) alkylamino or halogen provided that at least one of the residues B or B' is substituted or unsubstituted phenyl or B and B' together form an adamantane residue.

Furthermore this printed publication mentions that ultraviolet absorbers or stabilizers like hindered amine functions (HALS) or singulet oxygen removers can be added to the photochromic compounds in order to improve the stability and the lifetime.

Photochromic naphthopyrans having an amide substituent, which can be a acyclic amide, at the 9-position of the basic naphthopyran structure are known from PCT/WO 95/00867. This substitution causes the absorption maximum to shift into the longwave range but also results in diminished maximum darkening and slower darkening velocity.

DESCRIPTION OF THE INVENTION

The object of the present invention is the description and the synthesis of photochromic compounds which possess improved properties compared to the compounds known from the state of the art, such as a good photochromic effect, a high darkening velocity, intense maximum darkening, a longwave absorption in the activated state, a rapid lightening velocity and a long lifetime.

An element of the present invention was understanding that suited for solving this object :is a photochromic compound, which has a diaryl-3H-naphthopyran structure having at the 8-position a cyclic nitrogen base linked via a nitrogen atom, having the following structure:

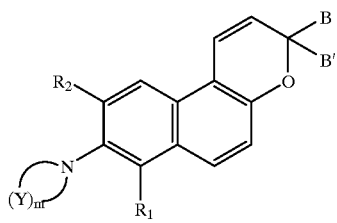

with
R1 and R2: hydrogen, $C_1$–$C_4$ alkyl or $C_1$–$C_4$ alkoxy
B and B':

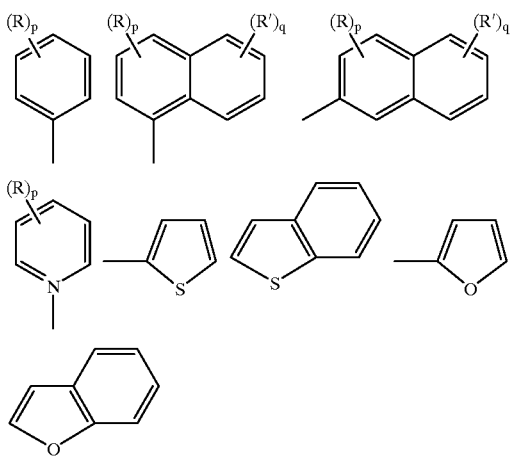

with R and R':
$C_1$–$C_4$ alkyl, $C_1$–$C_4$ halogen alkyl, $C_1$–$C_4$ alkoxy, $C_1$–$C_4$ alkoxy ($C_1$–$C_4$) alkyl, di($C_1$–$C_5$, alyklamino, halogen, with halogen=F, Cl, Br
and p, q: 0, 1, 2
Y: —O—, —S—, N—R" with R"=$C_1$–$C_6$ alkyl, phenyl, benzyl
—(CZ$_2$)—,
with Z=H, $C_1$–$C_6$ alkyl, and two Z also together $C_5$–$C_7$ cycloalkyl
and m being an integer from 3 to 7
with at least (m–1) residues Y being —(CZ$_2$)—.

These compounds are superior in various respects to the compounds known from the state of the art.

The invented introduction of a cyclic nitrogen base at the 8 position of the diaryl-3H-naphthopyran improves the electron stabilizing effect of the substituents known from the state of the art, such as by way of example —OR, due to a stronger electron donator effect of the cyclic nitrogen base. This increased stabilization surprisingly leads only to a small shift of the absorption maximum of the non-activated form of the photochromic compound but to a great bathochromic shift of the absorption maximum of the activated form of the photochromic compound.

The introduction of a cyclic nitrogen base instead of analog compounds having an open amine structure known from the state of the art improves the lifetime of the photochromic compound.

Especially advantageous is if, according to claim 2, a class of compounds known as hindered amine light stabilizer (HALS) is introduced at the 8-position of the diaryl-3H-naphthopyran structure. These substances, whose effect is based on the capture and inactivation of radicals, are utilized as light protection means in polymer materials. The conventionally employed HALS have two essential structural features. First, they have a free amine function (N—H), and second they possess steric hindrance, greatly space-filling groups in the immediate vicinity of this free amine function.

Recently, polymer substances of the HALS type have also been developed. These polymer substances of the HALS type no longer have a free amine function, but rather are polymerized via a substituent at the nitrogen. However, like the conventional HALS they possess steric hindrance groups at the ortho-position for the amine function. Although the light protective effect of these new substances does not attain the quality of conventional HALS having a free amine function, it suffices for using these substances in the embodiment of the present invention described in claim 2.

The introduction of the HALS substances into the basic diaryl-3H-naphthopyran structure by means of the N-atom linked cyclic nitrogen base occurs according to the present invention in such a manner that the ring of the cyclic nitrogen base is provided with the HALS properties. In addition to the N-atom, which represents the linking point to the diaryl-3H-naphthopyran structure, the cyclic nitrogen base has an amine function and at the ortho-position to this amine group it has a greatly space-filling substituent, such as by way of illustration tetramethyl, tert.-butyl or other branched or long-chain groups.

The use of these substances, which are known as HALS substances, for light stabilization is described for instance in EP 0313 941 A1 or in the journal "farbe+lack", 95. Jahrgang, 10/1989, pp. 715 ff. Das Taschenbuch der Kunststoff Additive by Gächter/Müller, 2nd edition, Carl Hanser Verlag, describes on pp. 144 ff. the use of these HALS as additives for polymer mixtures.

However, on the basis of this literature, known is only to add the substances to the polymer materials. None of the documents, however, mentions entering these compounds in a modified form of a cyclic nitrogen base into other molecules, such as by way of illustration photochromic dyestuffs.

The described HALS compounds, which for example are obtainable under the tradenames TINUVIN, CHIMASORB, CYASORB; SPINUVEX or HOSTAVIN, are usually added to the photochromic compounds in concentrations of 0.01 to 5% in order to increase their lifetime.

Introducing these substances directly into the diaryl-3H-naphthopyran structure at the 8-position, an N-atom linked cyclic nitrogen base from the hindered amine light stabilizer (HALS) compound, obviates adding these stabilizers later, thereby facilitating the use of the invented compounds in the manufacture of plastic articles having photochromic properties. The lifetime of the photochromic compounds is also improved, because the stabilizer is entered directly into the molecule. Undesired effects such as wrong dosage or demixing are thus prevented. In this way it is always ensured that an active HALS is always located in the vicinity of the dyestuff molecule. In conventional addition, this requires very high concentrations, which are partly no longer soluble in the monomer.

Just as advantageous is to add the HALS compounds not immediately into the cyclic nitrogen base, but rather link them as a substituent directly or via an alkyl bridge —(CX2)n—, with X=H, $C_1$–$C_6$ alkyl, and n is an integer from 0 to 6, to the cyclic nitrogen base.

Moreover, it was recognized that suited for solving the object of the present invention are also substances which have a cyclic nitrogen base like the type of the HALS compounds which is linked via an alkyl bridge— $(CX_2)_n$, with X=H, $C_1$–$C_6$ alkyl, and is an integer from 0 to 6, with one N-atom being linked at the 8-position of the diaryl-3H-naphthopyran structure. The third valence of the N-atom can be free or can be substituted by C1–$C_6$ alkyl.

Although in this way the electron stabilizing properties of the cyclic nitrogen base are slightly weakened by the greater distance to the diaryl-3H-naphthopyran structure, the invented compounds are superior to the state of the art compounds due to the simultaneously occurring light-stabilizing effect of the HALS compound.

Furthermore, as described the cyclic nitrogen base can also have a condensated on aromatic or heteroaromatic system or a condensated-on cycloalkyl ring.

Examples for the cyclic nitrogen bases, which are introduced at the 8-position of the diaryl-3H-naphthopyran structure via the N-atom are azetidine, pyrrolidine, piperidine, hexahyroazepine, heptamethylimine, morpholine, thiomorpholine, N-methylpiperazine, N-phenylpiperazine, indoline, isoindoline, benzoindoline, tetrahydrochinoline, tetrahydroisochinoline and N-methylimidazolidine.

What is claimed is:

1. A photochromic compound with a diaryl-3H-naphthopyran structure and an N-atom linked cyclic nitrogen base at the 8-position, having the formula

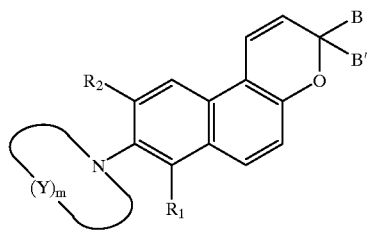

with $R_1$ and $R_2$: hydrogen, $C_1$–$C_4$ alkyl or $C_1$–$C_4$ alkoxy,

B and B':

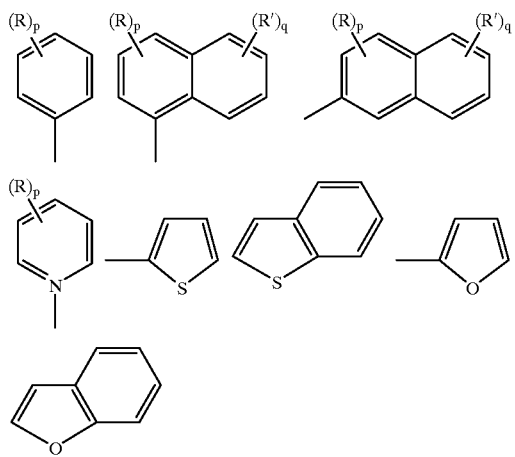

with R and R': $C_1$–$C_4$ alkyl, $C_1$–$C_4$ halogen alkyl, $C_1$–$C_4$ alkoxy, $C_1$–$C_4$ alkoxy ($C_1$–$C_4$) alkyl, di($C_1$–$C_5$) alkylamino, halogen, with halogen=F, Cl, Br; and p and q: 0, 1, 2, Y: —O—, —S—, N—R" with R"=$C_1$–$C_6$ alkyl, phenyl or benzyl, or —(CZ$_2$)—, with Z=H or $C_1$–$C_6$ alkyl, and two Z also together=$C_5$–$C_7$ cycloalkyl, wherein R" or one Z may be a hindered amine light stabilizer (HALS) compound or a hindered amine light stabilizer compound linked via an alkyl bridge —(CX$_2$)n—, with X=H or $C_1$–$C_6$ alkyl, and n is an integer from 0 to 6; and m: an integer from 3 to 7, with at least (m−1) of the groups Y being —(CZ$_2$)—.

2. A photochromic compound with a diaryl-3H-napthopyran structure, wherein that said compound has at the 8-position an N-atom linked cyclic nitrogen base derived from a hindered amine light stabilizer (HALS) compound.

3. A photochromic compound with a diaryl-3H-naphthopyran structure and an N atom linked nitrogen base at the 8 position, said compound having the formula

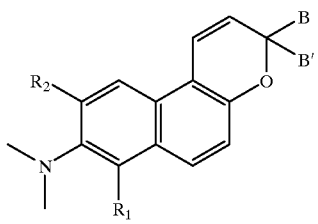

with

R1 and R2: hydrogen, $C_1$–$C_4$ alkyl or $C_1$–$C_4$ alkoxy;

B and B':

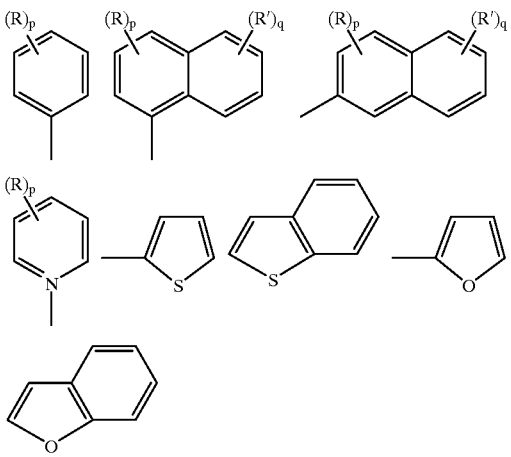

with R and R': $C_1$–$C_4$ alkyl, $C_1$–$C_4$ halogen alkyl, $C_1$–$C_4$ alkoxy, $C_1$–$C_4$ alkoxy ($C_1$–$C_4$) alkyl, di($C_1$–$C_5$) alkylamino, halogen=F, Cl, Br; and p and q: 0, 1, 2:

wherein the N-atom in the 8-position is linked to a hindered amine light stabilizer (HALS) compound via an alkyl bridge —(CX$_2$)$_n$—, with X=H or $C_1$–$C_6$ alkyl, and n is an integer from 0 to 6, the N-atom having as a further substituent H or $C_1$–$C_6$ alkyl.

4. A photochromic compound according to claim 1, wherein said cyclic nitrogen base at the 8-position has been ring-condensed with an aromatic, heteroaromatic or cycloalkyl ring.

5. A photochromic compound according to claim 1, wherein said cyclic nitrogen base is azetidine.

6. A photochromic compound according to claim 1, wherein said cyclic nitrogen base is pyrrolidine.

7. A photochromic compound according to claim 1, wherein said cyclic nitrogen base is piperidine.

8. A photochromic compound according to claim 1, wherein said cyclic nitrogen base is hexahydroazepine.

9. A photochromic compound according to claim 1, wherein said cyclic nitrogen base is heptamethylimine.

10. A photochromic compound according to claim 1, wherein said cyclic nitrogen base is morpholine.

11. A photochromic compound according to claim 1, wherein said cyclic nitrogen base is thiomorpholine.

12. A photochromic compound according to claim 1, wherein said cyclic nitrogen base is N-methylpiperazine.

13. A photochromic compound according to claim 1, wherein said cyclic nitrogen base is N-phenylpiperazine.

14. A photochromic compound according to claim 4, wherein said cyclic nitrogen base is indoline.

15. A photochromic compound according to claim 4, wherein said cyclic nitrogen base is isoindoline.

16. A photochromic compound according to claim 4, wherein said cyclic nitrogen base is benzoindoline.

17. A photochromic compound according to claim 4, wherein said cyclic nitrogen base is tetrahydroquinoline.

18. A photochromic compound according to claim 4, wherein said cyclic nitrogen base is tetrahydroisoquinoline.

19. A photochromic compound according to claim 1, wherein said cyclic nitrogen base is N-methylimidazolidine.

20. A photochromic compound according to claim 2, wherein said cyclic nitrogen base is 2,2,6,6-tetramethylpiperazine and is linked via said nitrogen atom with said diaryl-3H-naphthopyran at the 4-position.

* * * * *